United States Patent
Bergmann et al.

(10) Patent No.: US 7,977,072 B2
(45) Date of Patent: Jul. 12, 2011

(54) SANDWICH IMMUNOASSAY FOR IDENTIFYING PARTIAL PROANP PEPTIDES

(75) Inventors: Andreas Bergmann, Berlin (DE); Joachim Struck, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 467 days.

(21) Appl. No.: 10/535,875

(22) PCT Filed: Oct. 16, 2003

(86) PCT No.: PCT/EP03/11597
§ 371 (c)(1), (2), (4) Date: Dec. 5, 2005

(87) PCT Pub. No.: WO2004/046181
PCT Pub. Date: Jun. 3, 2004

(65) Prior Publication Data
US 2006/0234295 A1    Oct. 19, 2006

(30) Foreign Application Priority Data
Nov. 20, 2002   (DE) .................................. 102 54 149

(51) Int. Cl.
G01N 33/00  (2006.01)
G01N 33/53  (2006.01)
G01N 33/543 (2006.01)
G01N 33/541 (2006.01)
G01N 21/00  (2006.01)

(52) U.S. Cl. .......... 435/86; 435/7.94; 436/518; 436/164

(58) Field of Classification Search ........................ None
See application file for complete search history.

(56) References Cited

U.S. PATENT DOCUMENTS
5,498,524 A * 3/1996 Hall ................................ 435/7.1

FOREIGN PATENT DOCUMENTS
WO    WO 00/19207    4/2000

OTHER PUBLICATIONS

Missbichler et al. "Sandwich ELISA for proANP 1-98 facilitates investigation of left ventricular dysfunction" Eur J Med Res. Mar. 26, 2001;6(3):105-11.*
Arnlov et al. "N-terminal atrial natriuretic peptide and left ventricular geometry and function in a population sample of elderly males" J Intern Med. Jun. 2000;247(6):699-708.*
Merck Manuals Online Medial Library, section index for "Heart and Blood Vessel Disorders"; Home Edition, retrieved from www.merck.com/mmhe on Mar. 29, 2008.*
Bast et al. "Translational Crossroads for Biomarkers" Clin Cancer Res 2005; 11(17), 6103-6108.*
LaBaer et al. "So, You Want to Look for Biomarkers" Journal of Proteome Research 2005; 4, 1053-1059.*
Baker "In Biomarkers We Trust?" Nature Biotechnology 2005; 23(3), 297-304.*
Derwent, partial abstract translation for WO-00/19207 (5 pages), retrieved via East on Feb. 20, 2009.*
Harlow & Lane "Antibodies: A Laboratory Manual", Cold Spring Harbor Laboratory, Cold Spring Harbor, NY, 1988, pp. 23-24, 76, and 578.*
The Academic Press Dictionary of Science and Technology (definition for the term "polyclonal"; Oxford: Elsevier Science & Technology (1996); retrieved Oct. 22, 2008, from http://www.credoreference.com/entry/3144515/.*
Janeway et al. Immunobiology: the Immune System in Health and Disease (1999), Elsevier Science Ltd/Garland Publishing, New York, NY, Fourth Edition, pp. 34-35.*
Wolfe, S.L., Molecular and Cellular Biology, 1993, pp. 790-793.*
Mathis et al. "Probing Molecular Interactions with Homogeneous Techniques Based on Rare Earth Cryptates and Fluorescence Energy Transfer" Clin. Chem. 41/9, 1391-1397 (1995).*
Macaulay Hunter et al., "Analysis of peptides derived from Pro Atrial Natriuretic Peptide that circulate in man and increase in heart disease," Scandinavian Journal of Clinical and Laboratory Investigation, vol. 58, No. 3, pp. 205-216 (1998) Abstract Only attached.
Morgenthaler et al., "Immunoluminometric Assay for the Midregion of Pro-Atrial Natriuretic Peptide in Human Plasma," Clinical Chemistry, vol. 50, No. 1, pp. 234-236 (2004).
Itoh et al., "Peptides derived from atrial natriuretic polypeptide precursor in human and monkey brains," Journal of Hypertension, 6 (suppl 4) pp. S309-S319 (1988).
Meleagros et al., "Pro-Atrial Natriuretic Peptide (1-98): The Circulating Cardiodilatin in Man," Peptides, 10, pp. 545-550 (1989).
Buckley, et al., "Concentrations of N-terminal ProANP in human plasma: evidence for ProANP (1-98) as the circulating form," Clinica Chimica Acta, 191, pp. 1-14 (1990).
Lerman et al., "Circulating N-terminal atrial natriuretic peptide as a marker for symptomless left-ventricular dysfunction," Lancet, 341(8853), pp. 1105-1108 (1993).
Cleland et al., "Stability of plasma concentrations of N and C terminal atrial natriuretic peptides at room temperature," Heart, 75, pp. 410-413 (1996).
Hansen et al., "Proatrial natriuretic polypeptide (31-67) in healthy individuals: day-to-day variation and influence of sex and age," Scand J Clin. Lab. Invest., 55, pp. 447-452 (1995).
Overton et al., "Processing of Long-Acting Natriuretic Peptide and Vessel Dilator in Human Plasma and Serum," Peptides, 17(7), pp. 1155-1162 (1996).
Daggubati et al., "Adrenomedullin, endothelin, neuropeptide Y, atrial, brain, and C-natriuretic prohormone peptides compared as early heart failure indicators," Cardiovascular Research, 36, pp. 246-255 (1997).
Buckley et al., "Cardiac peptide stability, aprotinin and room temperature: importance for assessing cardiac function in clinical practice," Clinical Science, 97, pp. 689-695 (1999).
Klinge et al., "N-terminal proatrial natriuretic peptide in angina pectoris: impact of revascularization by angioplasty," International Journal of Cardiology, 68, pp. 1-8 (1999).

(Continued)

*Primary Examiner* — Nelson Yang
*Assistant Examiner* — Christine Foster
(74) *Attorney, Agent, or Firm* — Heslin Rothenberg Farley & Mesiti P.C.

(57) ABSTRACT

Disclosed is an improved sandwich immunoassay for identifying partial proANP peptides in cardiac and sepsis diagnosis by using two antibodies which specifically bond to partial sequences in the mid-regional area of NT-proANP, extending from amino acid 53 to amino acid 83 of NT-proANP.

7 Claims, 3 Drawing Sheets

OTHER PUBLICATIONS

Holmstrom et al., "Plasma levels of N-terminal proatrial natriuretic peptide in children are dependent on renal function and age," Scand J Clin Lab Invest, 60, pp. 149-159 (2000).

Franz et al., "N-terminal fragments of the proatrial natriuretic peptide in patients before and after hemodialysis treatment," Kidney International, 58, pp. 374-383 (2000).

Hamer et al., "Enzyme Immunoassays for Fragments (Epitopes) of Human Proatrial Natriuretic Peptides," Clin Chem Lab Med, 38(1), pp. 27-32 (2000).

Cappellin et al, "Plasma atrial natriuretic peptide (ANP) fragments proANP (1-30) and proANP (31-67) measurements in chronic heart failure: a useful index for heart transplantation?," Clinica Chimica Acta, 310, pp. 49-52 (2001).

Jernberg et al., "Usefulness of Plasma N-Terminal Proatrial Natriuretic Peptide (proANP) as an Early Predictor of Outcome in Unstable Angina Pectoris or Non-ST-Elevation Acute Myocardial Infarction," The American Journal of Cardiology, 89, pp. 64-66 (2002).

Stridsberg et al., "A Two-site Delfia Immunoassay for Measurements of the N-terminal Peptide of pro-Atrial Natriuretic Peptide (nANP)," Upsala J. Med. Sci., 102, pp. 99-108 (1997).

Mitaka et al., "Plasma α-atrial natriuretic peptide concentrations in acute respiratory failure associated with sepsis: Preliminary study," Critical Care Medicine, 18(11), pp. 1201-1203, 1990.

Mitaka et al., "Endothelin-1 and atrial natriuretic peptide in septic shock," American Heart Journal, 126(2), pp. 466-468 (1993).

Marumo et al., "A Highly Sensitive Radioimmunoassay of Atrial Natriuretic Peptide (ANP) in Human Plasma and Urine," Biochemical and Biophysical Research Communications, 137(1), pp. 231-236 (1986).

Aiura et al., "Circulating concentrations and physiologic role of atrial natriuretic peptide during endotoxic shock in the rat," Critical Care Medicine, 23, pp. 1898-1906 (1995).

Mazul-Sunko et al., "Pro-atrial natriuretic peptide hormone from right atria is correlated with cardiac depression in septic patients," J. Endocrinol. Invest., 24, RC22-RC24 (2001).

Hartemink et al., "α-Atrial natriuretic peptide, cyclic guanosine monophosphate, and endothelin in plasma as markers of myocardial depression in human septic shock," Critical Care Medicine, 29(1), pp. 80-87 (2001).

Kiemer et al., "The atrial natriuretic peptide regulates the production of inflammatory mediators in macrophages," Ann Rheum Dis, 60, iii68-iii70 (2001).

Kiemer -et al., "The Atrial Natriuretic Peptide as a Regulator of Kupffer Cell Functions," Shock, 17(5), pp. 365-371 (2002).

Kiemer et al., "Induction of Iκb: atrial natriuretic peptide as a regulator of the NF-κB pathway," Biochemical and Biophysical Research Communications, 295, pp. 1068-1076 (2002).

Buckley et al., "N-terminal pro atrial natriuretic peptide in human plasma," Am. J. Hypertens, 3 (12) Pt. (1), pp. 933-935 (1990).

\* cited by examiner

SANDWICH IMMUNOASSAY FOR IDENTIFYING PARTIAL PROANP PEPTIDES

CROSS REFERENCE TO RELATED APPLICATIONS

This application is a 371 filing of PCT International application no. PCT/EP2003/011597 filed Oct. 16, 2003 and published in German as WO 2004/046181 on Jun. 3, 2004 which claims the priority of German application no. 102 54 149.3 filed Nov. 20, 2002, the disclosures of which are hereby incorporated by reference in their entirety.

The invention relates to methods for identifying partial proANP peptides or partial peptides formed therefrom in biological fluids for medical diagnosis, prognosis and therapy-accompanying monitoring by means of a sandwich immunoassay (two-sided immunoassay). In the context of the present Application, in particular the so-called NT-proANP or proANP (1-98) and partial peptides which contain a midregional partial sequence of this NT-proANP are referred to as "partial proANP peptides". The method according to the invention is used in particular in cardiac diagnosis and sepsis diagnosis, the term "diagnosis" usually being used below for the sake of simplicity as a general term which is also intended to include prognosis/early prognosis and therapy-accompanying monitoring.

It has long been known that, in cardiac diseases, in particular in the various phases of cardiac insufficiency and after myocardial infarctions, the hormone referred to as "atrial natriuretic peptide" (ANP, occasionally also referred to as atrial natriuretic factor, ANF) is secreted in increased amounts and, owing to numerous physiological effects, such as natriuresis, vasodilation, inhibition of renin and aldosterone secretion, plays an important role in the homoeostasis of the water balance and of the blood pressure. The atrial dilation is regarded as an important stimulus for ANP secretion in cardiac diseases.

Usually, a peptide comprising 28 amino acids (99-126) from the C-terminal segment of a prohormone comprising 128 amino acids (proANP; SEQ ID NO:2) is defined as the actual hormone ANP. On liberation of the ANP from the prohormone proANP, in addition to elimination of two amino acids (127/128) from the C-terminus thereof, the remaining larger partial peptides of the proANP, the N-terminal proANP consisting of 98 amino acids (NT-proANP; proANP (1-98)) is also released into the circulation in an equimolar amount. Since this NT-proANP has a substantially longer half-life or stability than ANP, NT-proANP can be used as laboratory parameters for the diagnosis, monitoring and therapy control in cardiac diseases. For further information, reference is hereby made to Lothar Thomas (Editor), Labor and Diagnose [Laboratory and Diagnosis], 5th extended edition, subsection 2.14 of Chapter 2., Kardiale Diagnostik [Cardiac Diagnosis], pages 116-118, and the literature cited therein.

Both for identifying ANP itself and for identifying NT-proANP in biological fluids (serum, plasma, urine), various immunoassays have in the past been developed and were used in clinical research and practice. The predominant part of immunoassays for ANP or NT-proANP identification is based on the known principle of competitive immunoassays, the most typical member of which in turn is radioimmunoassay (RIA). Competitive immunoassays identifying proANP or ANP are, for example, described or used in literature references 1. to 13. and 22. (RIA) and 14. and 15. (EIA) of the attached list of references.

Competitive immunoassays of the RIA or EIA type can, however, have a number of disadvantages which relate to practical handling and accuracy of measurement, particular disadvantages including non-optimum sensitivity, poor ruggedness, a greater susceptibility to cross-reaction and frequently also long measuring times. Since, in competitive immunoassays for identifying peptides (which represent analytes/reagents of the antigen type in the immunoassay), a procedure is furthermore adopted which employs an antibody (polyclonal or monoclonal) which specifically recognizes a certain partial peptide sequence which is present simultaneously in the analyte and in the immunoreagent used as competitor or for marking, the usual competitive assays recognize, as "immunoreactivity", only the presence of the respective partial peptide sequences, without in principle distinguishing whether this sequence is part of a shorter or longer peptide. If, however, different competitive immunoassays of this type are used with antibodies which bind to different segments of a known sequence of a longer polypeptide, it is possible, from the similarity or difference of the measured results obtained, indirectly to derive whether in each case the same peptides were measured by means of the different competitive immunoassays or whether the peptide sequences recognized were parts of different molecular peptide species, for example of degradation products. Different degradation products may, on the one hand, be the result of different competing degradation reactions. However, even if only a single degradation route is taken, and all degradation products originate from one and the same precursor peptide, different concentrations of different partial peptides and fragments can be observed. If in fact the measured samples contain degradation products which are formed at different rates or as such have different stabilities (lifetime), different concentrations are determined for the different species, even if these can form primarily only in equimolar amounts owing to their origin from one and the same peptide.

By using different antibodies which recognize different sequences of the NT-proANP (proANP 1-98; SEQ ID NO:1) for identifying NT-proANP with the aid of competitive immunoassays, it was found that various peptides which correspond to degradation products of the NT-proANP (proANP 1-98) occur in biological fluids, in particular blood or urine. In particular, it was found that fragments having a relatively low molecular weight, in particular those to which the amino acid sequences (1-30, 31-67 and 79-98) of the proANP were assigned on the basis of their immunoreactivity, are formed from NT-proANP (cf. for example the literature references 3., 6., 7., 8., 9., 13., 14. and 15. of the attached list of literature references).

Competitive immunoassays which specifically recognize said sequences always recognize in the same manner—if influences of different avidities or possible conformative influences are neglected—also the complete NT-proANP and therefore do not distinguish between this and its respective fragments.

In comparison with competitive immunoassays, non-competitive sandwich immunoassays (two-sided immunoassays) have a number of advantages, including the fact that they can be better designed than solid-phase assays (heterogeneous assays), may be more rugged in terms of handling, may give measured results with a higher sensitivity and are also more suitable for automation and series measurement. In addition, in comparison with competitive immunoassays which operate with only one type of antibody, they can also provide somewhat different information, in that sandwich immunoassays recognize only those molecules or peptides in which both binding sites for the antibodies used for sandwich formation are present on the same molecule. If the binding sites are present, for example, on different partial peptides (degradation products, fragments), binding of the antibodies to such fragments does not lead to a measured signal typical of the complete "sandwich".

Owing to the known advantages of sandwich immunoassays generally and owing to the possibility of selectively measuring only the complete NT-proANP without the measurement being influenced by degradation products and fragments, sandwich immunoassays for identifying NT-proANP have also already been described and used in clinical research and practice. Thus, EP 721 105 B1 describes a sandwich immunoassay for identifying proANP, in particular in the diagnosis of cardiac diseases and of chronic renal failure, in which two monoclonal antibodies are used, one of which binds to the amino acids 1-25 of the proANP (cf. EP 350 218 B1) and the other to the amino acids 43-66 of the proANP. With such a sandwich immunoassay, only those partial proANP peptides which contain the first 25 amino acids of the proANP sequence are detected or are detected together with proANP (1-98).

A further sandwich immunoassay similar in this respect is described in the publication (Stridsberg) mentioned as No. 18 in the attached list of literature references. This sandwich immunoassay, too, operates with two monoclonal antibodies, one of which binds to the amino acids 1-30 of the proANP while the other binds to the amino acids 79-98. Owing to the choice of the binding sites at the ends of the proANP (1-98), it is to be assumed that only the intact proANP (1-98) is detected by means of this sandwich immunoassay.

Furthermore, WO 00/19207 describes a method for identifying proANP 1-98, which method employs two out of three polyclonal antibodies which bind to the amino acid sequences 8-27, 31-64 and 79-98 of the sequence of the proANP (1-98). The assay for identifying proANP (1-98), which is offered commercially by the Applicant of WO 00/19207, is an enzyme immunoassay which employs a pair of affinity-purified polyclonal sheep antibodies, of which the antibody used in immobilized form recognizes the amino acids 10-19 of the proANP, while a second polyclonal antibody which recognizes the amino acids (85-90) is used for the detection (cf. operating instructions for the proANP (1-98) sandwich assay from BIOMEDICA; A-1210 Vienna). This assay, too, therefore detects only those peptide species which contain end segments of the complete proANP (1-98), i.e. the complete NT-proANP.

All assays of the prior art which operate competitively or according to the sandwich principle were developed substantially as assays which were intended for cardiac diagnosis or were used in cardiac diagnosis, chronic renal failure also being mentioned as a further facility for diagnostic use (cf. EP 721 105 B1 and literature reference 29 of the attached list of literature references).

WO 00/22439 of the Applicant describes for the first time the occurrence of significantly increased concentrations of proANP also in sera and plasmas of sepsis patients. proANP was identified in the exploratory experiments described by using a commercially available RIA kit in which the binding to an antibody was determined according to the competitive measuring principle, which antibody recognized amino acids 26-55 of the so-called preproANP which, compared with the proANP at the N-terminus, is longer by a signal peptide comprising 25 amino acids. The peptide species detected in the determinations described in WO 00/22439 was or were not characterized in more detail. In particular, no investigation was carried out to determine whether the species detected was a shorter partial peptide of the N-terminus of the proANP, whether it was the complete NT-proANP or whether, in analogy to the increased occurrence of procalcitonin observed in the case of sepsis but not detectable in the circulation in healthy subjects, a longer species was measured, which was the entire proANP (1-128) or at least comprised substantial parts thereof.

From the investigations into the occurrence of procalcitonin which has in the meantime been established as a sepsis and inflammation marker (cf. EP 656 121 B1 or U.S. Pat. No. 5,639,615 or, for example, a review of subsequent discoveries by W. Karzai et al., in Infection, Vol. 25 (1997), pages 329-334; DE 101 19 804 A1 and a number of further patent applications of the Applicant on the subject of sepsis diagnosis, which were not yet published at the time of filing of the present Patent Application), it is known that, in sepsis, which may be regarded as a systemic infection or systemic inflammatory process, many physiological processes, in particular numerous enzyme activities, take place in greatly changed form, which results, in the circulation during sepsis, in the discovery of numerous biomolecules which are not detectable in healthy subjects and which are also not formed or not formed in this form in other pathological processes. Thus, for example, procalcitonin is usually a precursor of the hormone calcitonin, which does not enter the circulation. In the case of sepsis, however, greatly increased serum and plasma concentrations of procalcitonin are found without increased calcitonin concentrations simultaneously being observable. Against the background of such discoveries, rapid interpretations of medical findings in the laboratory on the basis of analogy are ruled out when, in the case of sepsis, detection methods respond to biomarkers which are already known per se from other contexts. It must always be expected that, in the case of sepsis, other molecular species have entered the circulation, and other proteolytic degradation mechanisms have been activated, than in the case of other diseases, in particular noninfectious and noninflammatory diseases.

Recently, some further papers have been published which confirmed the detection of proANP in sepsis (cf. literature references 24. and 25. of the attached list of literature references). The occurrence of proANP is interpreted primarily as a consequence of the disturbed cardiovascular activity during sepsis. However, it is of interest that other more recent papers (cf. 26. to 28. of the attached list of literature references) report that the hormone ANP also appears to perform important functions in the immune system, and that ANP performs regulatory functions within the reaction cascade of an inflammatory process.

In order to be able to investigate more thoroughly the clinical relevance of increased proANP or NT-proANP concentrations in sepsis on the basis of reliable measured data, the Applicant thought it to be desirable to have available an immunodiagnostic assay method which does not have the known disadvantages of competitive assay methods and which is less dependent than the known sandwich immunoassays on whether the species detected in the patient's body fluid is the complete NT-proANP or comprises the complete N-terminus of the NT-proANP.

The Applicant therefore decided to provide a novel sandwich immunoassay for identifying proANP or partial peptides derived therefrom, which immunoassay, in contrast to such immunoassays known to date, does not operate with antibodies which recognize the termini of the NT-proANP but with antibodies which both bind in a midregional area of the NT-proANP. Surprisingly, the sandwich immunoassay obtained not only proved to be substantially more sensitive than the previously known commercial sandwich immunoassays with regard to proANP identification in sepsis diagnosis but also exhibited substantially improved sensitivity in the area of cardiac diagnosis. In the present Application, sensitivity is defined—as usual—in such a way that with a sensitivity of 100% in a determination, all persons suffering from the disease are correctly identified as positive; the definition of specificity is accordingly that, with a specificity of 100%, all healthy subjects are correctly identified as negative and no healthy subjects are incorrectly identified as positive.

The present invention therefore relates, according to claim 1, to a method for identifying proANP or partial peptides formed therefrom, which are not the C-terminal ANP, in biological fluids for medical diagnosis, prognosis and therapy-accompanying monitoring by means of a sandwich immunoassay (two-sided immunoassay) using two antibodies which specifically bind to different partial sequences of the NT-proANP, which is characterized in that both antibodies bind to partial sequences in the midregional area of the NT-proANP, which extends from about amino acid 50 to amino acid 90, in particular from amino acid 53 to 83, of the NT-proANP.

The antibodies may be monoclonal and/or polyclonal antibodies but are preferably affinity-purified polyclonal antibodies.

Particularly preferably, one of the antibodies is obtained by immunizing an animal, in particular a sheep, with an antigen which contains a synthetic peptide sequence which has the amino acids 53-72 of the proANP and an additional cysteine residue at the N-terminus, and the other antibody is correspondingly obtained with an antigen which contains a synthetic peptide sequence which has the amino acids 73-90 or 73-83 of the proANP with an additional cysteine residue at the N-terminus. The antibodies obtained using said synthetic peptides, which together represent a complete midregional segment of the proANP sequence, thus recognize only binding sites in the area of amino acids 53-83 of the NT-proANP and, in the form of polyclonal antibodies, they can completely detect said area.

In a preferred embodiment, the method is carried out as a heterogeneous sandwich immunoassay, in which one of the antibodies is immobilized on an arbitrary solid phase, for example the walls of coated test tubes (e.g. of polystyrene; "coated tubes"; CT) or on microtitre plates, for example of polystyrene, or on particles, for example magnetic particles, while the other antibody carries a residue which represents a directly detectable label or permits selective linkage to a label and serves for detection of the sandwich structures formed. Delayed or subsequent immobilization using suitable solid phases is also possible.

In principle, all marking techniques which can be used in assays of the type described are employed, including marking with radio isotopes, enzymes, fluorescent, chemoluminescent or bioluminescent labels and directly optically detectable colour markers, such as, for example, gold atoms and dye particles, as used in particular for so-called point-of-care (POC) or accelerated tests. In the case of heterogeneous sandwich immunoassays, the two antibodies may also have parts of a detection system of the type described below in connection with homogeneous assays.

It is therefore within the scope of the present invention also to design the method according to the invention as an accelerated test.

The method according to the invention can furthermore be designed as a homogeneous method in which sandwich complexes formed from the two antibodies and the proANP or partial proANP peptide to be detected remain suspended in the liquid phase. In such a case, it is preferable to mark both antibodies with parts of a detection system which, when both antibodies are integrated into a single sandwich, permit signal generation or signal triggering. Such techniques can be designed in particular as fluorescence amplification or fluorescence extinction detection methods. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively determines only reaction products which contain both marking components in a single immune complex, directly in the reaction mixture. As an example, reference may be made to the technology which is offered under the brands TRACE® (Time Resolved Amplified Cryptate Emission) or KRYPTOR® and implements the teachings of the above-mentioned Applications.

It was surprisingly found that, according to the invention, with the use of two antibodies, in particular two affinity-purified polyclonal antibodies which both bind in the midregional area, i.e. in the area of the amino acids from about 50 to 90, in particular 53-83, of the sequence of the NT-proANP, an assay having substantially improved sensitivity compared to commercially available assays of the sandwich type is obtained. This statement applies, as will be shown below, not only to sepsis diagnosis but also to the area of cardiac diagnosis.

Particularly the last finding is surprising since numerous publications had disclosed that, on further proteolytic degradation of the NT-proANP, two further partial peptides which correspond to the amino acids 31-67 and 79-98 are formed in addition to a partial peptide corresponding to the amino acids 1-30 of the NT-proANP. The antibodies used in the method according to the invention thus bind to different degradation products from among the known NT-proANP degradation products.

It was by no means to be expected that, with the antibodies to be used according to the invention, it would be possible to achieve an improvement over other sandwich methods using antibodies which attack the termini of the NT-proANP (proANP 1-98). The literature does not describe any partial peptides of the NT-proANP which contain both binding sites for the antibodies according to the present invention but do not have the N-terminus used for binding all known sandwich immunoassays. Whether the substantially improved values for the assay sensitivity which are obtained according to the present invention are due to the degradation of the NT-proANP taking place according to a degradation scheme not described to date or whether the chosen binding sites are better accessible and/or permit stronger more selective binding or reproducible multiple marking and/or the degradation behaviour in the sample is influenced by the binding is to remain an open question. The interpretation of the substantial, experimentally demonstrated improved measured results is not part of the present invention.

It is assumed that the assay method according to the invention can also be particularly advantageously carried out in a so-called multiparameter diagnosis, in particular both in the area of cardiac diagnosis and in the area of sepsis diagnosis. Further parameters determined thereby are, for example, the cardiac parameters BNP or proANP or sepsis parameters which are selected, for example, from the group consisting of anti-ganglioside antibodies, the proteins procalcitonin, CA 125, CA 19-9, S100B, S100A proteins, LASP-1, soluble cytokeratin fragments, in particular CYFRA 21, TPS and/or soluble cytokeratin-1 fragments (sCY1F), the peptides inflamin and CHP, other peptide prohormones, glycine N-acyltransferase (GNAT), carbamoylphosphate synthetase 1 (CPS 1) and the C-reactive protein (CRP) or fragments thereof. In the case of said multiparameter assays, it is envisaged that the measured results for a plurality of parameters will be determined simultaneously or in parallel and, for example, will be evaluated with the aid of a computer program which also uses diagnostically significant parameter correlations.

The invention is explained in more detail below by a description of the preparation of the assay components, the procedure of a preferred embodiment of the assay and the results of proANP assays in EDTA plasmas of control persons and cardiac and sepsis patients, obtained using the assay according to the invention.

Reference is made to figures which show the following:

EXPERIMENTAL SECTION

Materials and Methods

Figure 1:
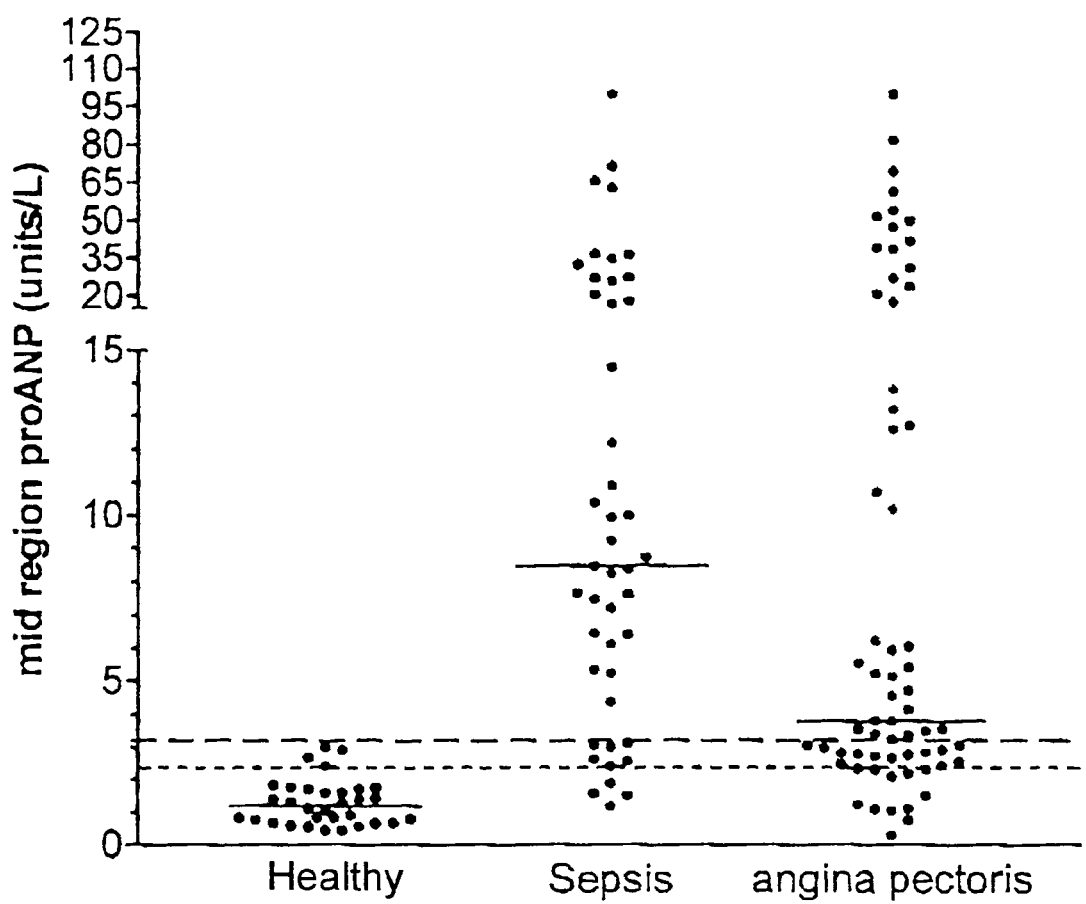
FIG. 1 shows the identification of proANP in a control group of healthy persons, a group of sepsis patients and a group of Angina Pectoris patients with the aid of the proANP assay according to the invention.

Initially two segments of the known amino acid sequence of the proANP (SEQ ID NO:2) or of human NT-proANP (SEQ ID NO:1), which corresponded to positions 53-72 and 73-90 thereof, respectively, were chosen for obtaining the antibodies. On the basis of the results of an epitope mapping, a sequence 73-83 shortened at the C-terminal end was subsequently used in the final antibody recovery instead of the sequence 73-90. All segments, supplemented with an N-terminal cysteine residue, were chemically synthesized as soluble peptides by standard methods, purified, subjected to quality control by means of mass spectrometry and reversed phase HPLC and subjected to lyophilization in aliquots (the work was carried out on behalf of the Applicant by JERINI AG, Berlin, Germany). The amino acid sequences of the synthetic peptides are as follows:
Peptide "MPCL21" (positions 53-72; SEQ ID NO:3): CPEVPPWTGEVSPAQRDGGAL
Peptide "SPCL19" (positions 73-90; SEQ ID NO:4): CGRGPWDSSDRSALLKSKL
Peptide "SPCL12" (positions 73-83; SEQ ID NO:5): CGRGPWDSSDRS
Immunization For immunization purposes, the peptides MPCL21 and SPCL19 were conjugated by means of MBS (m-maleimidobenzoyl-N-hydroxysuccinimide ester) to the carrier protein KLH (keyhole limpet haemocyanin), the operating instructions "NHS ester maleimide crosslinkers" from PIERCE, Rockford, Ill., USA, being followed.

With the conjugates obtained, sheep were immunized according to the following scheme: each sheep initially received 100 μg of conjugate (the stated masses are based on the peptide fraction of the conjugate) and then in each case 50 μg of conjugate at 4 week intervals. Beginning with the 4th month after the beginning of immunization, 700 ml of blood were taken from the sheep at 4 week intervals, and antiserum was obtained therefrom by centrifuging.

Conjugations, immunization and recovery of antisera were carried out on behalf of the Applicant by MicroPharm, Carmarthenshire, UK.

Purification of the Antibodies

In a one-step method, the peptide-specific antibodies were prepared from the antisera which had been obtained from the 4th month after immunization.

For this purpose, first the peptides MPCL21 and SPCL19 and subsequently, instead of the latter, the shorter peptide SPCL12 were coupled to SulfoLink Gel according to the operating instructions of the manufacturer ("SulfoLink Kit", from PIERCE, Rockford, Ill., USA). In each case 5 mg of peptide were used per 5 ml of gel for the coupling.

The affinity purification of antibodies specific against the two peptides MPCL21 and SPCL19 or SPCL12 and obtained from the sheep antisera was carried out as follows:

The respective SulfoLink gels were introduced into separation columns. The peptide columns obtained were first washed 3 times alternately with 10 ml each of elution buffer (50 mM citric acid, pH 2.2) and binding buffer (100 mM sodium phosphate, 0.1% Tween, pH 6.8). 100 ml of the antisera were filtered over a 0.2 μm filter and the respective peptide-coupled gel was added to said antisera, which gel was for this purpose rinsed quantitatively with 10 ml of binding buffer from the column in which it had been washed. The incubation of peptide-coupled gel with the antisera was effected overnight at room temperature in a shaking flask. Thereafter, the batches were transferred quantitatively into empty columns (NAP 25, Pharmacia, emptied). The outflowing material was discarded. They were then washed protein-free with 250 ml of binding buffer (see above) (the protein content of the wash eluate exhibited an absorption at 280 nm of less than 0.02). Elution buffer was then added to the washed columns, and the eluate was collected in 1 ml fractions. The protein content of each fraction was determined by means of the BCA method (bicinchoninic acid; cf. PIERCE Chemical Technical Library, www.piercenet.com). Fractions 4-7 were pooled, and yields of 15.5 mg for the anti-MPCL21 antibody and of 20.7 mg for the anti-SPCL12 antibody were obtained in the protein determination of the pooled fractions by means of the BCA method.

In an epitope mapping of the antibodies obtained in the manner described, it was found that affinity-purified antibodies which were obtained with the peptide SPCL19 bound virtually exclusively to epitopes in the area of amino acids 73-83, i.e. a segment corresponding to the peptide SPCL12. The peptide SPCL19 was therefore replaced by the peptide SPCL12 in the affinity purification.

Marking

For the preparation of a detection antibody, 500 μl of the polyclonal anti-MPCL21 antibody affinity-purified in the manner described were rebuffered over an NAP-5 gel filtration column (Pharmacia) in 1 ml of 100 mM potassium phosphate buffer (pH 8.0) according to the operating instructions. The protein concentration determination of the antibody solution gave a value of 1.5 mg/ml.

In order to provide this antibody with a chemiluminescent marker, 10 µl of MA70 acridinium NHS ester (1 mg/ml; from HOECHST Behring) were added to 132 µl of the antibody solution and incubation was effected for 15 min at room temperature. 358 µl of 1 M glycine were then added, and incubation was effected for a further 10 min. Thereafter, the marking batch was rebuffered over an NAP-5 gel filtration column (Pharmacia) in 1 ml of mobile phase A (1 mM potassium phosphate, 10% methanol, 0.1% Lubrol, 0.1% azide, pH 6.8) according to the operating instructions and was freed from low molecular weight constituents. In order to separate off final residues of label constituents not bound to antibody, an HPLC was carried out over hydroxylapatite (column: Knauer, 10 cm×8 mm ID, Ser. No. LF230 Batch No. 1250000A, hydroxylapatite Bio Rad 10 µm). The sample was applied and chromatography was effected at a flow rate of 1 ml/min by means of a linear mobile phase A/mobile phase B gradient. A solution of 500 mM potassium phosphate, 10% methanol, 0.1% Lubrol, 0.1% azide, pH 6.8, was used as mobile phase B. The wavelengths 280 nm and 368 nm were measured continuously using a flow photometer. The absorption ratio of 368 nm/280 nm reflects the degree of marking of the antibodies and was 0.16 at the peak.

The antibody-containing fractions, which eluted at about 40% of mobile phase B, were collected in 3 ml of 100 mM sodium phosphate, 150 mM NaCl, 5% bovine serum albumin (BSA), 0.1% sodium azide, pH 7.4.

This solution represents a tracer concentrate, which is used in the determinations described below.

Coupling

For the preparation of solid phase for the assay method according to the invention, irradiated 5 ml polystyrene tubes (from Greiner) were first coated with donkey anti-sheep IgG antibodies (from Scantibodies) as follows:

The antibody was diluted in 50 mM sodium phosphate, pH 6.5, to a concentration of 16.7 µg/ml. 300 µl of this solution were pipetted into each tube. The tubes were then incubated for 20 h at 22° C. The solution was filtered with suction, after which each tube was filled with 4.2 ml of 10 mM sodium phosphate, 2% Karion FP, 0.3% BSA, pH 6.5. After 20 hours, the solution was likewise filtered with suction.

The purified sheep antibody, which bound to the peptide SPCL12, was diluted in 50 mM sodium phosphate, 50 mM NaCl, 0.1% sodium azide, 0.05% BSA, pH 7.8, to a concentration of 4.3 µg/ml. 300 µl of this solution were pipetted into each tube. The tubes were then incubated for 20 h at 22° C., after which the solution was again filtered with suction. Each tube was then filled with 4.2 ml of 10 mM sodium phosphate, 2% Karion FP, 0.3% BSA, pH 6.5. After 20 h, the solution was filtered with suction. The tubes were then dried in a vacuum dryer.

Procedure for the Immunoassay According to the Invention and Evaluation of Said Immunoassay An assay buffer which had the following composition was used for the determinations:

100 mM sodium phosphate, 150 mM NaCl, 5% BSA, 0.1% unspecific sheep IgG, 0.1% sodium azide, pH 7.4.

An extract of an *E. coli* strain which expressed recombinant proANP (1-128) (InVivo GmbH, Hennigsdorf, Germany) served as standard material. This extract was serially diluted in horse normal serum (from SIGMA) for the preparation of standard solutions. Arbitrary proANP concentrations, corresponding to the dilutions of the standard material used, were assigned to the standard solutions thus prepared.

EDTA plasmas of apparently healthy persons, of sepsis patients and of patients with Angina Pectoris were measured as samples.

For this purpose, 200 µl of assay buffer and, in double determinations, 20 µl of the standards or samples were pipetted into the coated tubes in the first step of the determination. Incubation was then effected overnight at 22° C. with shaking. Thereafter, washing was effected 4 times with 1 ml of wash solution (0.1% Tween 20) per tube each time, and the tubes were allowed to drip. 200 µl of a 1:1000 dilution of the above tracer concentrate in assay buffer were then pipetted into each tube. Incubation was effected for 2 h at 22° C. with shaking. Thereafter, washing was effected 4 times with 1 ml of the above wash solution per tube each time, the tubes were allowed to drip and finally the chemiluminescence bound to the tubes was measured in a tailor-made manner in a luminometer (from BERTHOLD, LB952T; base reagents BRAHMS AG). Using the MultiCalc (spline fit) software, proANP concentrations of the samples were read from the standard curve.

The results obtained for the proANP determinations in EDTA plasmas of healthy persons (control samples), sepsis patients and patients with Angina Pectoris using the assay according to the invention are shown in FIG. 1. The cut-offs used are two threshold values which were chosen so that 100% of all healthy persons and 90% of all healthy persons, respectively, are detected as negative (measured values below the threshold value chosen as the cut-off).

Figure 2:
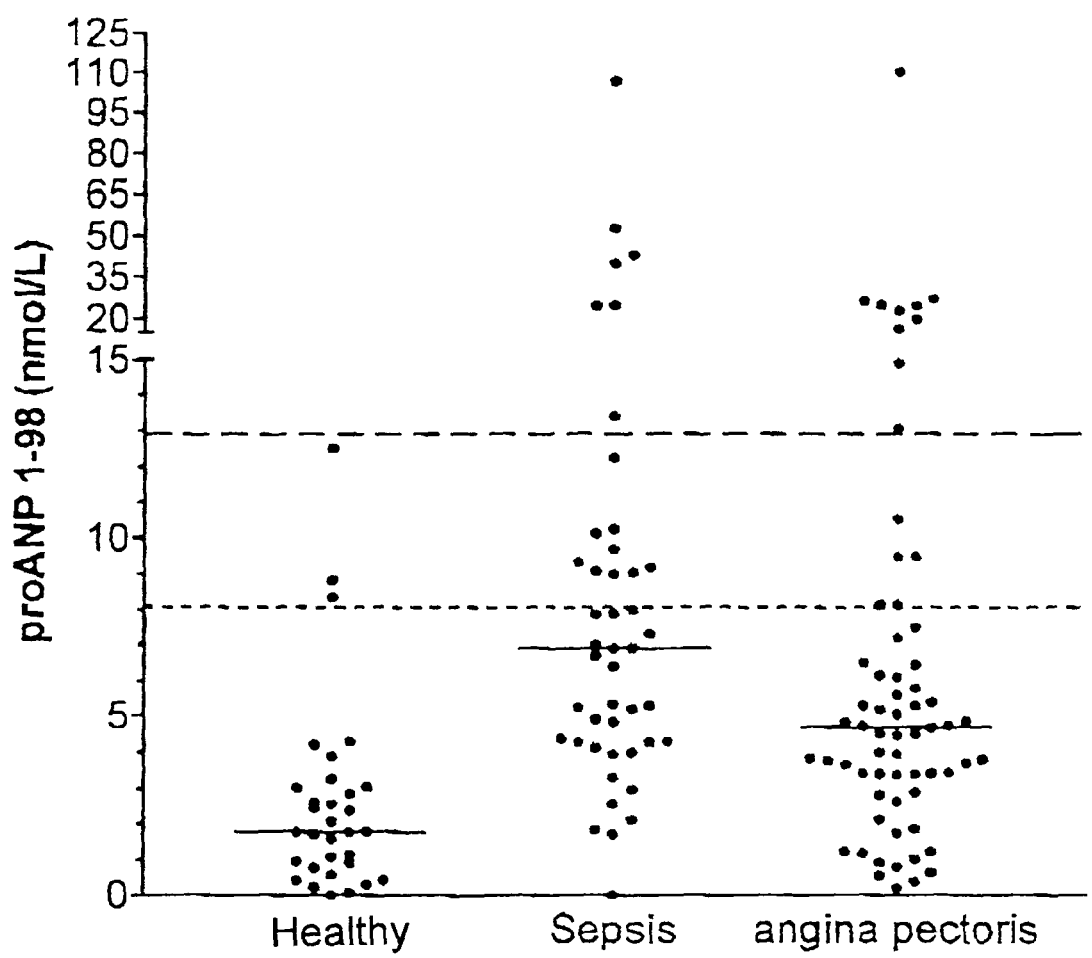
FIG. 2 shows corresponding measured results for the same samples as in FIG. 1, as obtained using a commercially available proANP sandwich assay in which two antibodies which bind to the amino acids 10-19 and 85-90 of the proANP are used.

The same samples were also measured using a commercially available sandwich assay according to the operating instructions of the manufacturer (operating instructions for proANP 1-98) sandwich assay from BIOMEDICA; A-1210 Vienna). The results are shown in FIG. 2, the cut-offs being established as a buffer.

Figure 3:
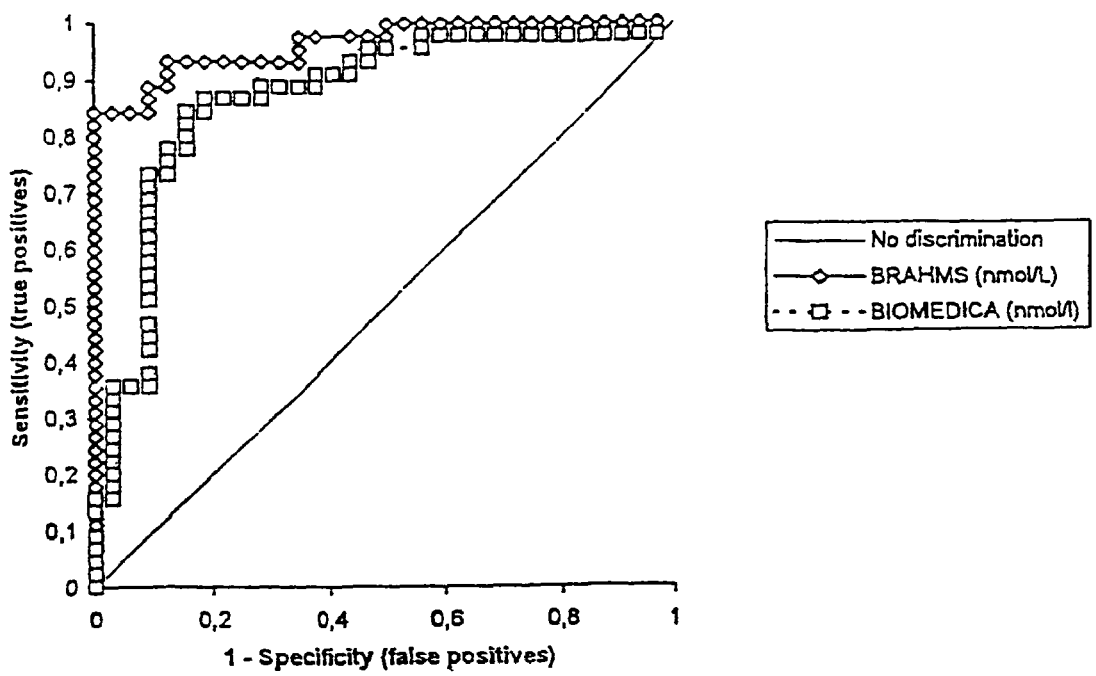
FIG. 3 shows so-called ROC curves (Receiver Operating Characteristic Plots) which show the sensitivities and specificities of the proANP assay according to FIGS. 1 and 2 in comparison. The diagram permits comparison of the value of the assays with the assays compared in the case of sepsis. In the case of ROC curves, the area between the relevant curve and a straight line at an angle of 45° ("area under the ROC function", AUC) can be taken as a characteristic of the statistical relevance of an assay.
Figure 4:
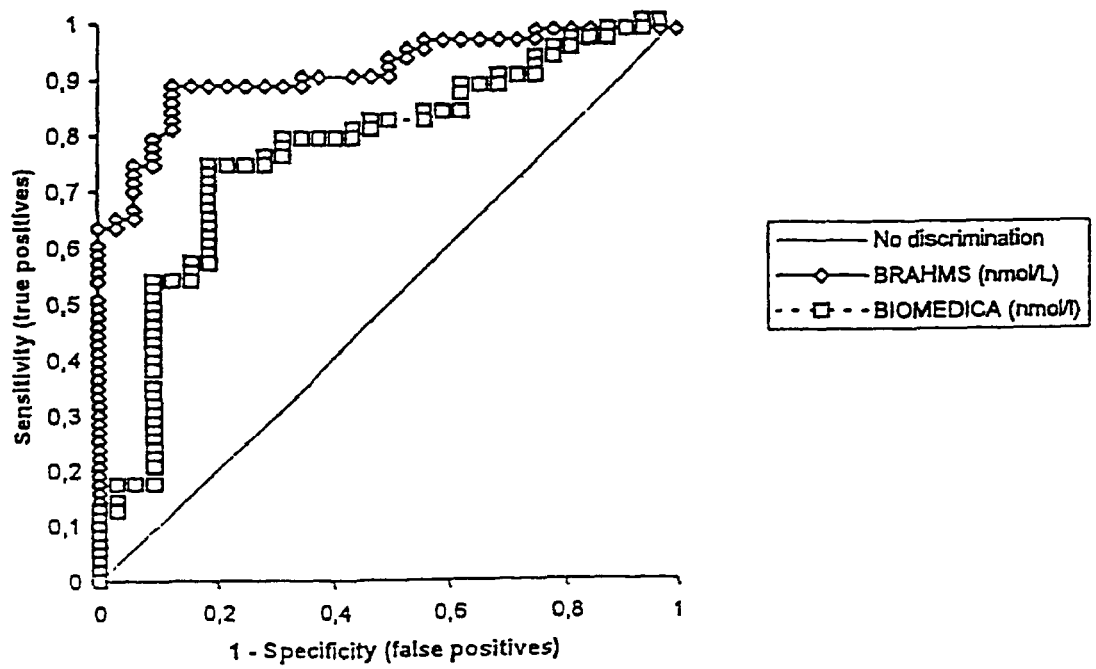
FIG. 4 shows a diagram which corresponds to FIG. 3 and permits a comparison of the value of the assays with the assays compared in the case of Angina Pectoris.

In FIG. 3, the results obtained with the two assays for the determinations in sepsis patients are compared using ROC curves, and the results for cardiac patients are compared in FIG. 4. If in each case the directly optically evident AUC values (cf. explanations for FIG. 3) of the respective ROC curves are used as a guide, it can immediately be seen that the method according to the invention gives measured values which are substantially superior with regard to their statistical relevance.

LIST OF REFERENCES

1. Hiroshi Itoh et al., Peptides derived from atrial natriuretic polypeptide precursor in human and monkey brains; Journal of Hypertension 1988, 6 (suppl 4) S309-S319;
2. L. Meleagros et al., ProAtrial Natriuretic Peptide (1-98): The Circulating Cardiodilatin in Man; Peptides, Vol. 10, 545-550, 1989
3. M. G. Buckley et al., Concentration of N-terminal ProANP in human plasma: evidence for ProANP (1-98) as the circulating form; Clinica Chimica Acta, 191 (1990) 1-14
4. Amir Lerman et al., Circulating N-terminal atrial natriuretic peptide as a marker for symptomless left-ventricular dysfunction; Lancet 1993; 341:1105-09, 1993
5. John G F Cleland et al., Stability of plasma concentrations of N and C terminal atrial natriuretic peptides at room temperature; Heart 1996; 75:410-413;
6. J. B. Hansen et al., Proatrial natriuretic polypeptide (31-67) in healthy individuals; day-to-day variation and influence of sex and age; Clin. Lab. Invest. 1995; 55:447-452
7. Rose M. Overton et al., Processing of Long-Acting Natriuretic Peptide and Vessel Dilator in Human Plasma and Serum; Peptides, Vol. 17, 1155-1162, 1996
8. Sreedevi Daggubati et al., Adrenomedullin, endothelin, neuropeptide Y, atrial, brain, and C-natriuretic prohormone peptides compared as early heart failure indicators; Cardiovascular Research 36 (1.997) 246-255
9. E. F. Macaulay Hunter et al., Analysis of peptides derived from Pro Atrial Natriuretic Peptide that circulate in man and increase in heart disease; Scand J Clin Invest 1998; 58: 205-216;
10. Martin G. Buckley et al., Cardiac peptide stability, aprotinin and room temperature: importance for assessing cardiac function in clinical practice; Clinical Science (1999) 97: 689-695
11. Randi Klinge et al., N-terminal proatrial natriuretic peptide in angina pectoris: impact of revascularization by angioplasty; International Journal of Cardiology 68 (1999), 1-8
12. H. Holmström et al., Plasma levels of N-terminal proatrial natriuretic peptide in children are dependent on renal function and age; Scand J Clin Invest 2000; 60: 149-160
13. Martina Franz et al., N-terminal fragments of the proatrial natriuretic peptide in patients before and after hemodialysis treatment; Kidney International, Vol. 58 (2000), 374-383
14. Engelbert Hartter et al., Enzyme Immunoassays for Fragments (Epitopes) of Human Proatrial Natriuretic Peptides; Clin Chem Lab Med 2000; 38(1):27-32
15. Enrico Cappelin et al., Plasma atrial natriuretic peptide (ANP) fragments proANP (1-30) and proANP (31-67) measurements in chronic heart failure; a useful index for heart transplantation? Clinica Chimica Acta 310 (2001) 49-52
16. Tomas Jernberg et al., Usefulness of Plasma N-Terminal Proatrial Natriuretic Peptide (proANP) as an Early Predictor of Outcome in Unstable Angina Pectoris or Non-ST-Elevation Acute Myocardial Infarction; The American Journal of Cardiology, Vol. 89, (2002), 64-66
17. Arbeitsanleitung zum Sandwichassay proANP (1-98) der Fa. BIOMEDICA; A-1210 Wien, Divischgasse 4 (2 affinitatsgereinigte polyklonale Ab gegen AS 10-19 und 85-90)
18. Mats Stridsberg et al., A Two-Site Delfia Immunoassay for Measurement of the N-terminal Peptide of pro-Atrial Natriuretic Peptide (nANP); in: Uppsala J. Med. Sci. 102; 99-108, 1997 (2 mAb gegen 1-30 und 79-98)
19. Lothar Thomas (Herausgeber), Labor und Diagnose, TH-Books, Frankfurt/Man, 5. erw. Auflage 2000, Seiten 114-118;
20. Chieko Mitaka et al., Plasma alpha-atrial natriuretic peptide concentration in acute respiratory failure associated with sepsis: Preliminary study; Critical Care Medicine, 1990, Vol. 18:1201-1203
21. Chieko Mitaka et al., Endothelin-1 and atrial natriuretic peptide in septic shock; American Heart Journal 1993; Vol. 126, No. 2, 466-468
22. Fumiaki Marumo et al., A Highly Sensitive Radioimmunoassay of Atrial Natriuretic Peptide (ANP) in Human Plasma and Urine; Biochem. Biophys. Res. Commun. 137: 231-236 (1985)
23. Koichi Aiura et al., Circulating concentrations and physiologic role of atrial natriuretic peptide during endotoxic shock in the rat; Critical Care Medicine 1995; 23:1889-1906
24. Mazul-Sunko et al., Pro-atrial natriuretic peptide hormone from the right atria is correlated with cardia depression in septic patients; J. Endocrinol. Invest 24; R22-R24, 2001
25. Koen J. Hartemink et al., alpha-Atrial natriuretic peptide, cyclic guanosine monophosphate, and endothelin in plasma as markers of myocardial depression in human septic shock; Critical Care Medicine 2001; 29:80-87
26. A K Kiemer et al., The atrial natriuretic peptide regulates the production of inflammatory mediators in macrophages; Ann Rheum Dis 2001; 60:iii68-iii70
27. Alexandra K. Kiemer et al., The Atrial Natriuretic Peptide as a Regulator of Kupffer Cell Function; Shock, Vol. 17, S. 365-371, 2002
28. Alexandra K. Kiemer et al., Induction of IκB: atrial natriuretic peptide as a regulator of the NF-κB pathway; Biochem. Biophys. Res. Commun. 295 (2002) 1068-1076
29. Buckley M G et al., N-terminal pro atrial natriuretic peptide in human plasma; Am. J. Hypertens. 1990 December; 3 (12Pt 1): 933-935.

The invention claimed is:

1. A method for detecting pro atrial natriuretic peptide (proANP) (SEQ ID NO: 2) and partial peptides of proANP comprising amino acids 53-90 of SEQ ID NO.:1, in a sample, said method comprising: a) contacting said sample with first antibodies consisting of antibodies that bind to a region of proANP consisting of amino acids 53-72 of SEQ ID NO.:1 and second antibodies consisting of antibodies that bind to a region of proANP consisting of amino acids 73-90 of SEQ ID NO.: 1, wherein at least one of said first and second antibodies is labeled with a detectable marker; b) detecting the amount of marker present in said sample, wherein the amount of marker correlates with the level of proANP and partial peptides of proANP comprising amino acids 53-90 of SEQ ID NO.: 1 in said sample.

2. The method of claim 1, wherein said first and second antibodies are both monoclonal antibodies, said first and second antibodies are both polyclonal antibodies, or either of said first and second antibodies is monoclonal and the other is polyclonal.

3. The method of claim 1, wherein said first and second antibodies are affinity-purified polyclonal antibodies.

4. The method of claim 1, wherein one of the antibodies is labeled with the detectable marker and the other is bound to a solid phase.

5. The method of claim 1, wherein both the first and the second antibodies are present in a reaction mixture and a first detectable marker based on fluorescence or chemiluminescence extinction or amplification is bound to the first antibodies, and a second detectable marker is bound to the second antibodies so that, after binding of said first and second antibodies to proANP and partial peptides of proANP comprising amino acids 53-90 of SEQ ID NO: 1 in the sample, a measurable signal is generated which permits detection of the resulting sandwich complexes in the reaction mixture.

6. The method of claim 5, wherein each of the detectable markers is selected from rare earth cryptates, chelates, fluorescent and chemiluminescent dyes.

7. The method of claim 1, wherein said second antibodies consist of antibodies that bind to a region of proANP consisting of amino acids 73-83 of SEQ ID NO: 1.

* * * * *

SEQUENCE LISTING

<160> NUMBER OF SEQ ID NOS: 5

<210> SEQ ID NO 1
<211> LENGTH: 98
<212> TYPE: PRT
<213> ORGANISM: Artificial Sequence
<220> FEATURE:
<223> OTHER INFORMATION: Description of Artificial Sequence: Synthetic
      fragment

<400> SEQUENCE: 1

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

```
Asp Arg Ser Ala Leu Leu Lys Ser Lys Leu Arg Ala Leu Leu Thr Ala
                85                  90                  95

Pro Arg

<210> SEQ ID NO 2
<211> LENGTH: 128
<212> TYPE: PRT
<213> ORGANISM: Homo sapiens

<400> SEQUENCE: 2

Asn Pro Met Tyr Asn Ala Val Ser Asn Ala Asp Leu Met Asp Phe Lys
 1               5                  10                  15

Asn Leu Leu Asp His Leu Glu Glu Lys Met Pro Leu Glu Asp Glu Val
                20                  25                  30

Val Pro Pro Gln Val Leu Ser Glu Pro Asn Glu Glu Ala Gly Ala Ala
            35                  40                  45

Leu Ser Pro Leu Pro Glu Val Pro Pro Trp Thr Gly Glu Val Ser Pro
        50                  55                  60

Ala Gln Arg Asp Gly Gly Ala Leu Gly Arg Gly Pro Trp Asp Ser Ser
 65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
               100                 105                 110

Ile Gly Ala Gln Ser Gly Leu Gly Cys Asn Ser Phe Arg Tyr Arg Arg
           115                 120                 125

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      fragment

<400> SEQUENCE: 3

Cys Pro Glu Val Pro Pro Trp Thr Gly Glu Val Ser Pro Ala Gln Arg
 1               5                  10                  15

Asp Gly Gly Ala Leu
            20

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      fragment

<400> SEQUENCE: 4

Cys Gly Arg Gly Pro Trp Asp Ser Ser Asp Arg Ser Ala Leu Leu Lys
 1               5                  10                  15

Ser Lys Leu

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      fragment
```

```
<400> SEQUENCE: 5

Cys Gly Arg Gly Pro Trp Asp Ser Ser Asp Arg Ser
  1               5                  10
```